(12) United States Patent
Behramand (10) Patent No.: US 12,209,070 B1
(45) Date of Patent: Jan. 28, 2025

(54) APPARATUS, COMPOSITIONS, AND METHODS FOR MAKING SOLID METHANE GAS

(71) Applicant: SNG International LLC, Seattle, WA (US)

(72) Inventor: Simak Behramand, Irvine, CA (US)

(73) Assignee: SNG International LLC, Seattle, WA (US)

(*) Notice: Subject to any disclaimer, the term of this patent is extended or adjusted under 35 U.S.C. 154(b) by 0 days.

(21) Appl. No.: 18/393,534

(22) Filed: Dec. 21, 2023

(51) Int. Cl.
*F25J 1/00* (2006.01)
*C07C 7/20* (2006.01)

(52) U.S. Cl.
CPC .............. *C07C 7/20* (2013.01); *F25J 1/0022* (2013.01); *F25J 2205/20* (2013.01); *F25J 2205/90* (2013.01)

(58) Field of Classification Search
CPC .............................. F25J 1/0022; F25J 2205/20
See application file for complete search history.

(56) References Cited

FOREIGN PATENT DOCUMENTS

CN 112742398 A * 5/2021 .............. B01J 23/83

OTHER PUBLICATIONS

Machine Translation of CN112742398A (Year: 2021).*
David L. Chander, A dirt-cheap solution? Common clay materials may help curb methane emissions. MIT News Office. Online Article. Jan. 10, 2022.

* cited by examiner

*Primary Examiner* — Ellen M McAvoy
*Assistant Examiner* — Ming Cheung Po
(74) *Attorney, Agent, or Firm* — Trojan Law Offices (57) ABSTRACT

The present invention is directed to a composition of solid methane gas that is stable at room temperature such that the solid methane gas is capable of storage and shipment without specialized equipment. The composition of solid methane gas is obtained by using a sophisticated apparatus and solid methane gas complexes having many different ingredients and ingenious methods. Methane gas flows through the sophisticated apparatus to be cooled and ultimately mixed with the solid methane bed complex at sub-zero Celsius conditions to create solid methane that is stable at room temperature. This solid methane is capable of being turned back into methane gas.

15 Claims, 9 Drawing Sheets

APPARATUS, COMPOSITIONS, AND METHODS FOR MAKING SOLID METHANE GAS

This application is a divisional application of U.S. patent application Ser. No. 17/746,870, filed on May 17, 2022, which issued as U.S. Pat. No. 11,873,460 on Jan. 16, 2024.

BACKGROUND OF THE INVENTION

Gas storage is both problematic and expensive. Natural gas goes to export plants and is liquified, often under pressure, over land, liquid natural gas (LNG) is transported through pipes. By sea, shipped by shipping container or similar. LNG takes up space, driving up logistical costs.

While fuel is stored at lower temperatures tends to present less of a hazard, it can be extremely expensive and difficult to store and transport, especially across borders. Thus, while storing fuel at lower temperatures has its benefits, attempts to store natural gas at low temperature are wrought with significant drawbacks. Further, solid state matter takes up less volume than liquid or gas. As such, there is a need for a way to transport natural gas at normal temperatures and with less space. Therefore, there is a need for a way of producing solid natural gas that is stable at normal temperatures and is capable of transport without specialized equipment.

SUMMARY

The present invention is directed to a process that efficiently and economically produces solid methane gas capable of storage and shipment without specialized equipment. The process includes an apparatus for preparing solid methane gas, a method for using the apparatus, and a method for preparing mixtures for use with the apparatus. The apparatus is made of affordable components in a reusable composition.

The apparatus for preparing solid methane gas includes a drum storing the natural gas connected to a cooling case housing a coolant which reacts to generate cold. The temperature of the gas is reduced by passing through the coolant. The gas passing through the coolant is isolated within a pipe. The pipe is non-linear, thus allowing more gas to be exposed to the coolant. The cooling case has an outlet for both natural gas and coolant. The cooling case has an intake for used cycled coolant to be re-chilled. The cooling case gas output is connected to a gas storage container.

The gas storage container is preferably a double input tank with diving valves at each end. Pressure in the gas storage container drives gas through the cooling case and into the gas storage container. Piped gas within the cooling case first passes through a manometer before entering the gas storage container. A cryogenic jacket surrounds the gas storage container.

The cooling case is connected by a hose to the gas storage container cryogenic jacket. A pump lies along the coolant hose line. The motor drives coolant from the cooling case into and circulating through said gas storage container jacket. This coolant cycling further cools gas within the gas storage container. The gas storage container cryogenic jacket has a coolant output through which used coolant returns to the cooling case.

The liquid gas repository is connected to a chamber where liquid natural gas meets prepared solid matter. The chamber also has a cooling jacket. The chamber contains a door at a base through which a solid methane bed complex enters the chamber. The chamber is removably connected to a vacuum that removes air once the solid methane bed complex is placed in the chamber and the door closed. The vacuum created inside the chamber helps draw liquified gas in from the gas storage container. During vacuuming a filter keeps the solid methane bed complex within the chamber. The chamber contains conical particles that slow gas molecular movement. This furthers the cooling process as liquid gas proceeds toward a solid state. The chamber has a cryogenic jacket connectable to the cooling case. The chamber cryogenic jacket operates the same way as the gas storage container jacket.

The chamber has a mixing shaft that partially enters said chamber at an end opposite the chamber base. The shaft has a handle on an end external to said chamber. The shaft has a mixing impeller on an end opposite the handle located within the chamber. The impeller keeps a gas-solid complex in motion during mixing. The chamber is internally lined with an anti-sparking layer to facilitate interface between the chamber and impeller. Said layer is fixed to a chamber body with adhesive.

Method for Using Solid Methane Gas Apparatus

A method for using said apparatus prepares solid methane gas in shapes that can be tailored to consumer storage needs. A variant of this method comprises preparing a solid methane bed complex, placing said complex in a chamber, sealing the chamber, and then vacuuming air from said chamber before proceeding with gas and coolant flow.

A methane source, natural gas, is secured within a pressurized drum. Then a coolant is prepared by combining ice and salt. Refrigerant gases can also be used. Coolant is contained in a cooling case. Natural gas flows from the drum to and through the cooling case. Inside the cooling case gas flows, isolated from the coolant, through a pipe. Piped gas exits the cooling case and proceeds to a manometer, then to a liquid gas storage container. Liquid gas then flows to a chamber for mixing with the prepared solid methane bed complex. Cryogenic jackets surround the gas storage container and the chamber to facilitate cooling through the process. A pump drives coolant via industrial hose through each jacket. The gas-solid methane bed complex mixing proceeds for 24 hours, followed by drying a product.

The method uses coolant and pressure to slow molecules from gas to liquid. In addition to cool temperature and pressure, physical arrays within the chamber and properties of the solid methane bed complex facilitate transition of the natural gas from liquid to solid.

Method for Preparing Solid Methane Bed Complex

Solid methane bed complex is prepared by assembling a solid methane bed mix containing any one primary reagent of calcium sulfate, calcium oxide, or magnesium chloride. A primary reagent is mixed with an elegant reagent blend at atmospheric pressure and temperature. Once the solid methane bed complex is produced,

BRIEF DESCRIPTION OF THE DRAWINGS

These and other features and advantages of the present invention will become appreciated, as the same becomes better understood with reference to the specification, claims and drawings herein:

DETAILED DESCRIPTION OF THE INVENTION

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

It will be understood that when an element is referred to as being "on" another element, it can be directly on the other element or intervening elements may be present there between. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section.

As used herein, the singular forms "a," "an," and "the," are intended to include the plural forms as well, unless the context clearly indicates otherwise. It will be further understood that the terms "comprises" and/or "comprising," "includes" and/or "including," and "have" and/or "having," when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom," and "upper" or "top," and "inner" or "outer," may be used herein to describe one element's relationship to another elements as illustrated in the Figures. It will be understood that relative terms are intended to encompass different orientations of the device in addition to the orientation depicted in the figures.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing.

An Apparatus for Making Solid Methane Gas

Figure 1:
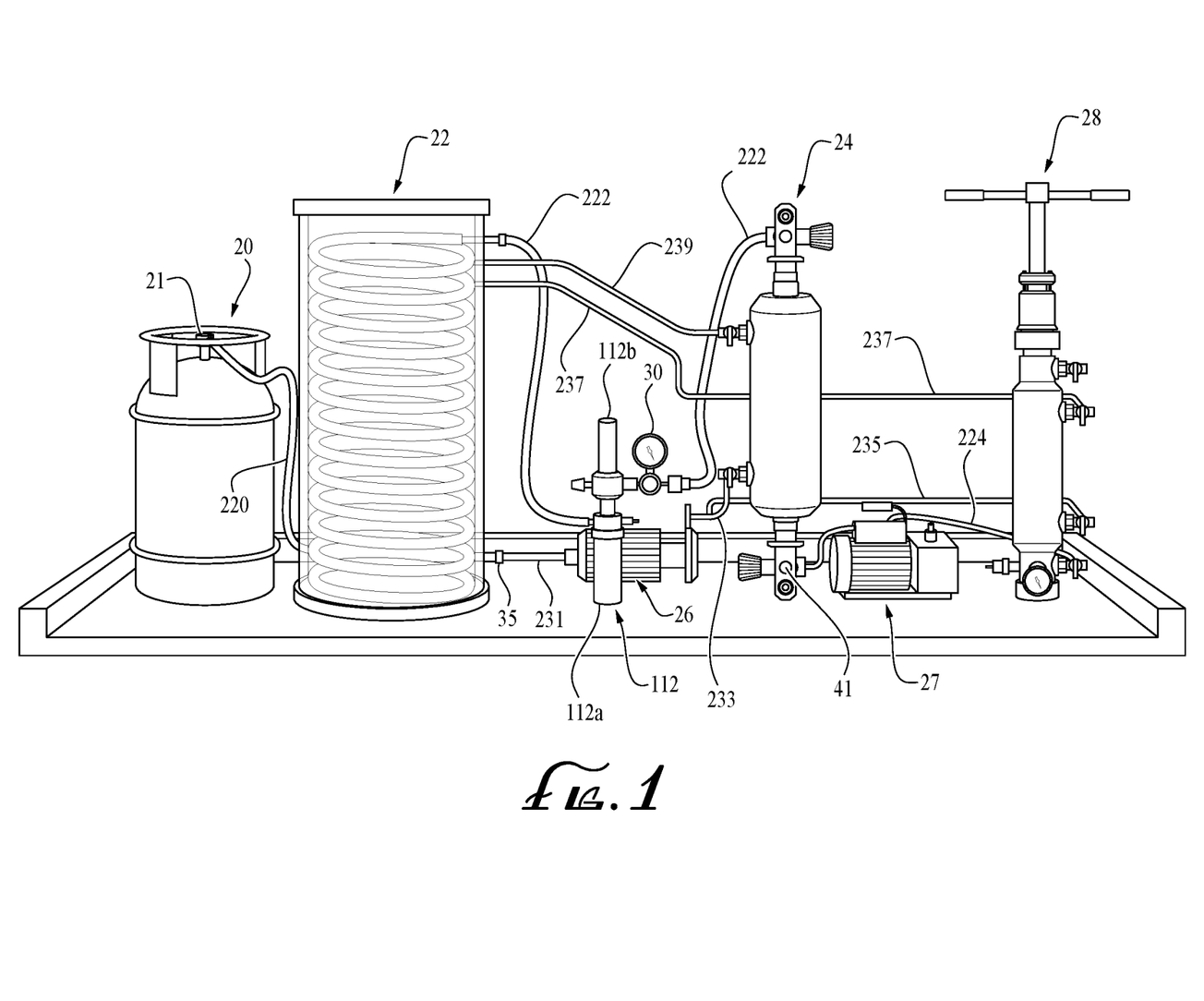
FIG. 1 shows the front side of an apparatus for making solid methane in accordance with a first embodiment of the present invention.
Figure 1A:
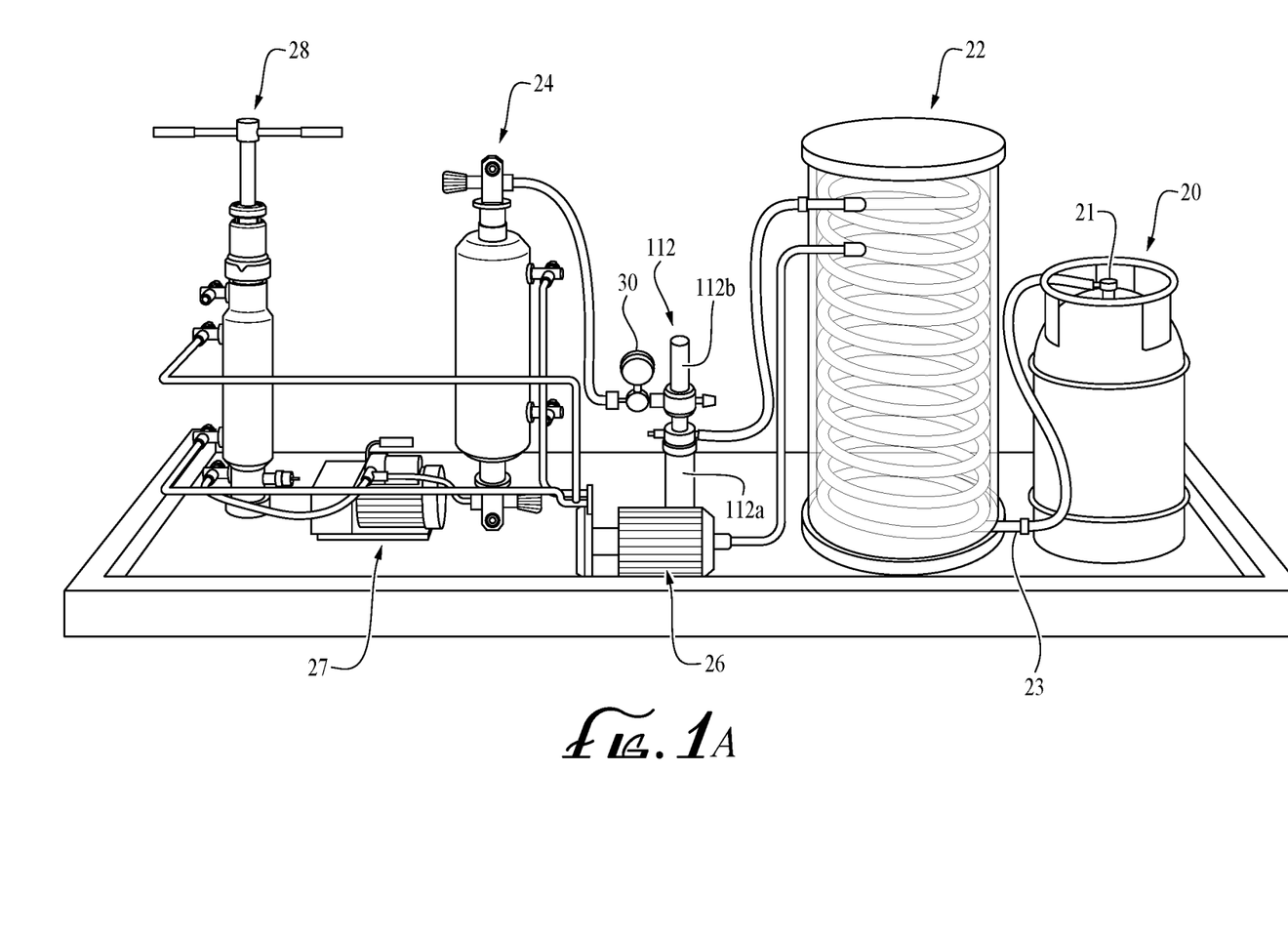
FIG. 1A shows another embodiment of the apparatus in FIG. 1 from the back side to display hose line configuration.

An apparatus for producing solid methane is disclosed herein. As shown in FIGS. 1-1A, the apparatus generally includes a drum 20, a cooling case 22, a gas storage container 24, a pump 26, a chamber 28, a vacuum 27, and a manometer 112. Generally, the gas storage container 24 is enclosed by a gas storage container cryogenic jacket 40 and the chamber 28 is enclosed by a chamber cryogenic jacket 102. The drum 20 may be a standard fuel natural gas drum with a gas drum valve 21. The drum 20 is configured to contain natural gas and is connected to the cooling case 22 by a first hose 220. The first hose 220 is connected to the cooling case 22 by a cooling case gas input 32 which is connected to a pipe 34 contained in the cooling case 22. The natural gas flows through the first hose 220 into the pipe 34 contained in the cooling case 22. The drum 20 serves as the first gas input of the system and pressurizes natural gas. Liquid natural gas is preferably used in the system. Other gases may be used without departing from the concepts disclosed herein.

The cooling case 22 includes a coolant cavity 38 having a coolant and the pipe 34. The natural gas flows through the pipe 34 which isolates said natural gas from the coolant contained within the cooling case 22. A second hose 222 is connected to a cooling case gas output 36, thereby connecting the pipe 34 to a gas storage container 24. The natural gas flows through this second hose 222.

Figure 2A:
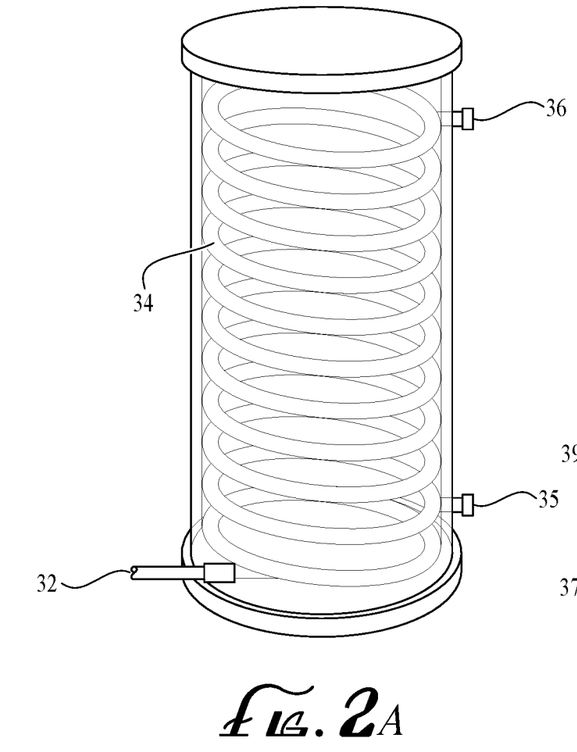
FIG. 2A shows a front facing embodiment of the cooling case shown in FIG. 1.
Figure 2B:
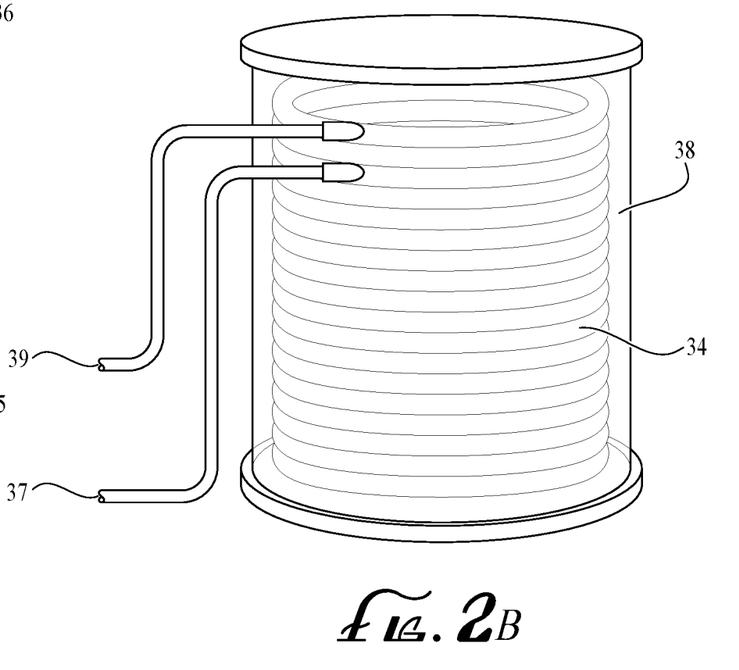
FIG. 2B shows a rear facing embodiment of the cooling case shown in FIG. 1.

FIGS. 2A and 2B depict a front and back view of the cooling case 22. The cooling case 22 contains the coolant cavity 38 filled with coolant through which the pipe 34 traverses. The coolant is configured to bring the temperature of the inside of the cooling case 22 to subzero Celsius conditions, preferably −20° C. In some embodiments, the temperature may range between −10° C. and −20° C. The cooling case 22 preferably includes two coolant intakes 37 and 39 configured to recapture coolant in the system and replace it into the cooling case 22. These coolant intakes 37 and 39 recapture coolant from the gas storage container cryogenic jacket 40 and the chamber cryogenic jacket 102. The cooling case 22 also preferably includes a cooling case coolant output 35. The coolant output 35 is configured to allow coolant to exit the coolant cavity 38 and flow to the gas storage container cryogenic jacket 40 and the chamber cryogenic jacket 102. While the locations of the cooling gas input 32, cooling gas output 36, coolant intakes 37 and 39, and coolant output 35 may vary on the cooling case 22, it is preferable to have the cooling gas input 32 located at the bottom of the cooling case 22 and the cooling gas output 36 located at the top of the cooling case 22. It is also preferable to have the coolant output 35 located at the bottom of the cooling case 22 close to the pump 26, and the coolant intakes 37 and 39 at the top of the cooling case 22.

The pipe 34 may be constructed out of aluminum or copper, preferably aluminum. Copper pipes cool more quickly but are more susceptible to breaking. Aluminum pipes are sturdier under cooling case conditions thus better suited to large embodiments of this invention. The pipe 34 is preferably configured to maximize pipe length through the cooling cavity 38. Greater pipe length extends the duration that gas flowing within is subjected to cooling case temperatures thereby facilitating gas liquification. In one embodiment the pipe 34 maybe coiled. In other embodiments the pipe 34 may be squared or circular, or variations thereof. The pipe 34 maybe oriented vertically, horizontally, or variations thereof.

As shown in FIG. 1, the gas storage container 24 is enclosed by the gas storage container cryogenic jacket 40. A third hose 231 connects the coolant cavity 38 to a pump 26 via the coolant output 35, which in turn is connected to the gas storage container cryogenic jacket 40 by a fourth hose 233. An eighth hose 239 connects the gas storage cryogenic jacket 40 back to the cooling cavity 38 via the coolant intake 39. Coolant flows from the coolant cavity 38 through the third hose 231 to the pump 26, the pump 26 to the fourth hose 233, the fourth hose 233 into the gas storage container cryogenic jacket 40, the cryogenic jacket 40 to the eighth hose 239, and back into coolant cavity 38 though the coolant intake 39.

A manometer 112 and a gas flow indicator 30 intersects the second hose 222 running from the pipe 34 to the gas storage container 24. The gas storage container 24 is connected to the chamber 28 through a fifth hose 224. Natural gas flows through the fifth hose 224. The chamber 28 is enclosed by the chamber cryogenic jacket 102. The chamber cryogenic jacket 102 has a chamber cryogenic jacket coolant intake valve 104 and a chamber cryogenic jacket coolant output valve 106. The chamber cryogenic jacket coolant intake valve 104 is connected to the pump 26 via a sixth hose 235. A seventh hose 237 connects the chamber cryogenic jacket coolant output valve 106 to the cooling case at coolant intake 37. A vacuum 27 is detachably connected by the fifth hose 224 to the chamber 28. The chamber 28 has a mixing handle 118 and a replaceable chamber base 114.

The manometer 112 has a transparent chamber 112a. The transparent chamber 112a allows detection for whether gas flowing through the manometer 112 is in a gaseous or liquid state. A manometer gas release 112b serves as a gaseous gas expulsion site. If natural gas flowing through the manometer 112 is gaseous then the manometer gas release 112b is opened expelling the gas, then shut to prevent liquid from escaping. Gas may be recaptured at the gas release 112b for fuel efficiency.

In other embodiments, such as the embodiment shown in FIG. 1A, the circulation of the coolant throughout the system is maintained between the pump 26, gas storage container cryogenic jacket 40, and the chamber cryogenic jacket 102. In these embodiments, the coolant does not flow back to the cooling case 22. In other embodiments, especially embodiments using refrigerant gases as the coolant, the coolant will not need to be circulated throughout the system, instead being wholly contained individually in the coolant cavity 38, gas storage container cryogenic jacket 40, and chamber cryogenic jacket 102. The remainder of the system remains the same for these alternative embodiments.

Figure 3:
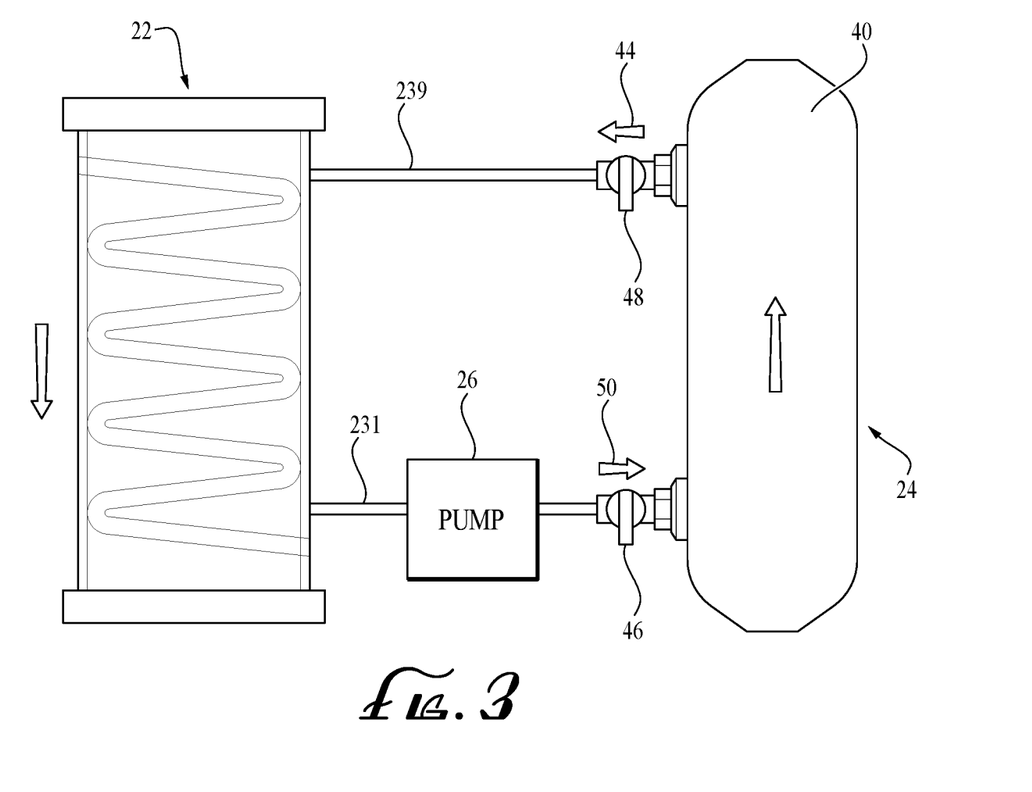
FIG. 3 shows a coolant circulation path between the cooling case and the gas storage container cryogenic jacket as shown in FIG. 1.

As shown in FIG. 3, the coolant flows from the coolant cavity 38 through the coolant output 35 to the third hose 231, then to the pump 26. The pump 26 drives coolant through the fluid path as shown in FIG. 3 having the cooling case 22, pump 26, and gas storage container cryogenic jacket 40. The interior of the pump 26, third hose 231, and eighth hose 239 that contacts the coolant is preferably polyethylene or other anti-corrosive material. The pump 26 connects to a gas storage cryogenic jacket coolant intake valve 46 at the gas storage cryogenic jacket input 50. Coolant circulates through the gas storage container cryogenic jacket 40 to maintain a cold temperature to keep natural gas in liquid state within the gas storage container 24. Used coolant exits the gas storage container cryogenic jacket 40 through a gas storage container cryogenic jacket output valve 48 at the gas storage container cryogenic jacket output 44. The coolant returns through the eighth hose 239 to the cooling case 22 at the cooling case coolant intake 39.

Figures 4A, 4B:
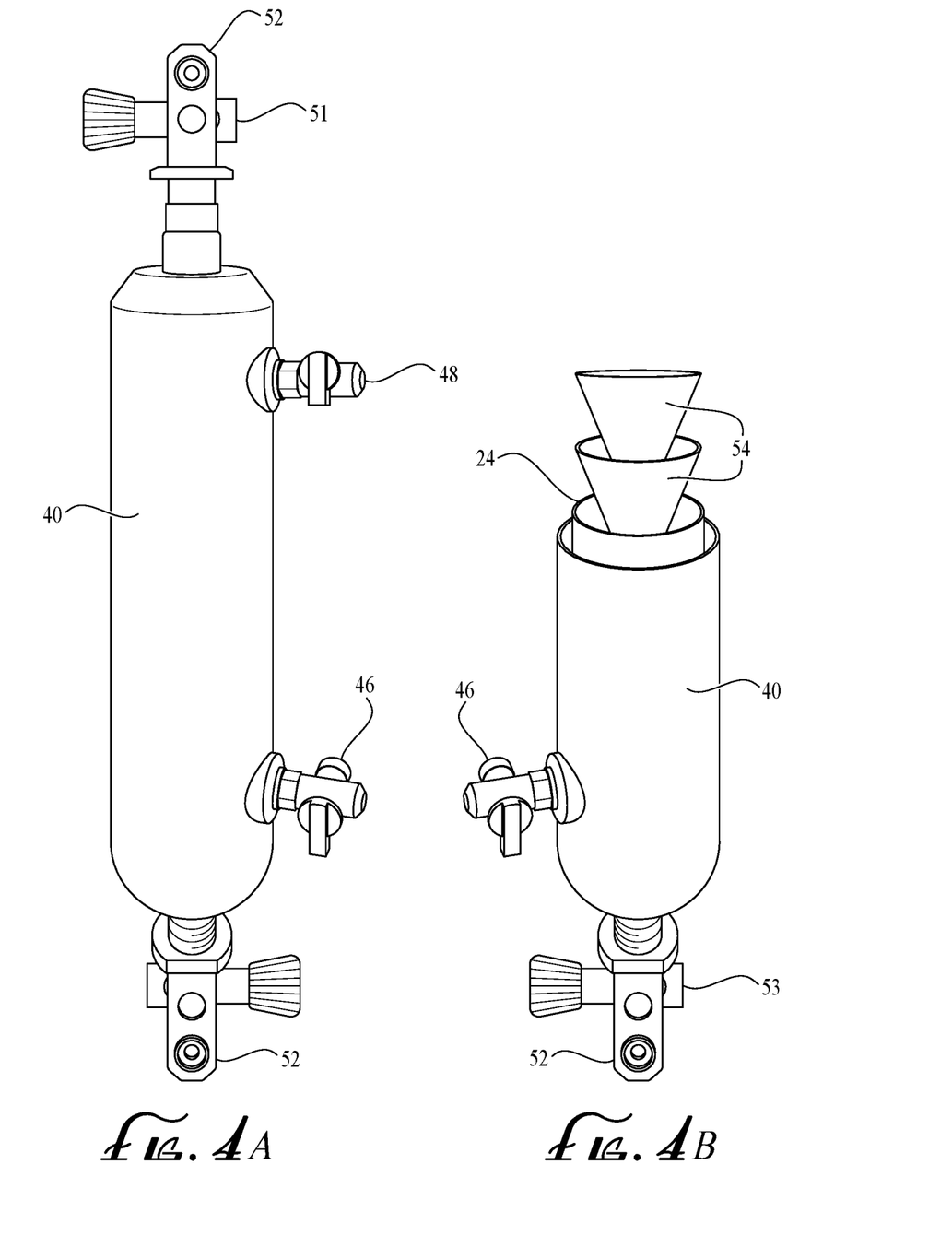
FIG. 4A shows the gas storage container as shown in FIG. 1.
FIG. 4B shows the internal components of the gas storage container shown in FIG. 4A.
Figure 5:
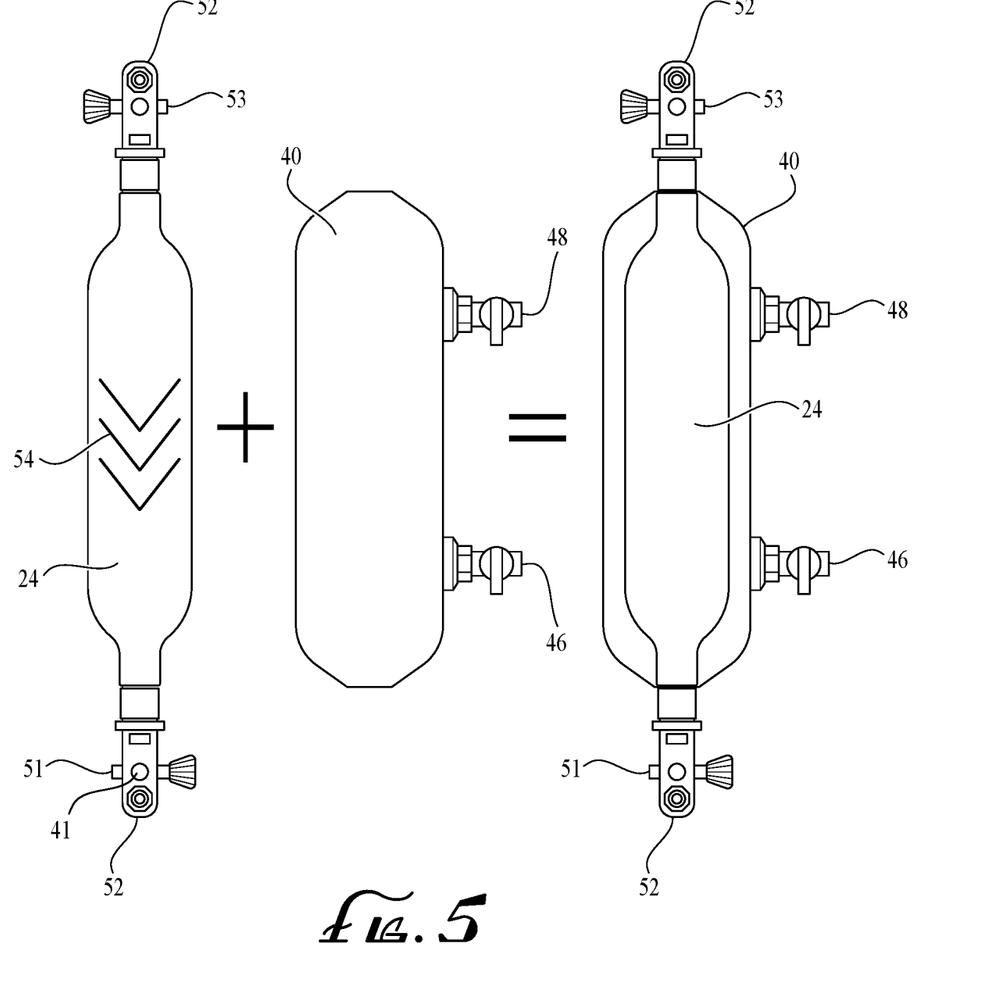
FIG. 5 shows the gas storage container and gas storage cryogenic jacket of FIG. 1.

As shown in FIGS. 4A, 4B, and 5, the gas storage container 24 cools and thereby slows the gas molecules passing through the gas storage container 24. This effect facilitates gas solidification in the chamber 28. The gas storage container 24 is preferably a long and narrow structure. In the preferred embodiment, the volume of the gas storage container 24 is 1 liter. This configuration efficiently maximizes gas proximity to coolant. This facilitates transition to increasingly dense physical states of gas matter. The gas storage container preferably has a gas storage container gas input 51 at an end of the gas storage container 24 and a gas storage container gas output 53 at another end. Molecular slowing is furthered by a particle array 54 that is placed within the gas storage container 24. The array is preferably of conical in shape. These sequential structures further slow the gas molecules while passing through the gas storage container 24.

Diving valves 52 at each gas input 51 and output 53 control gas entry and exit under pressure. Diving valves 52 open and close under pressures that standard valves cannot. While typical valves tolerate only up to 10 bar, the diving valves 52 tolerate pressures exceeding 120 bar.

Figure 6A:
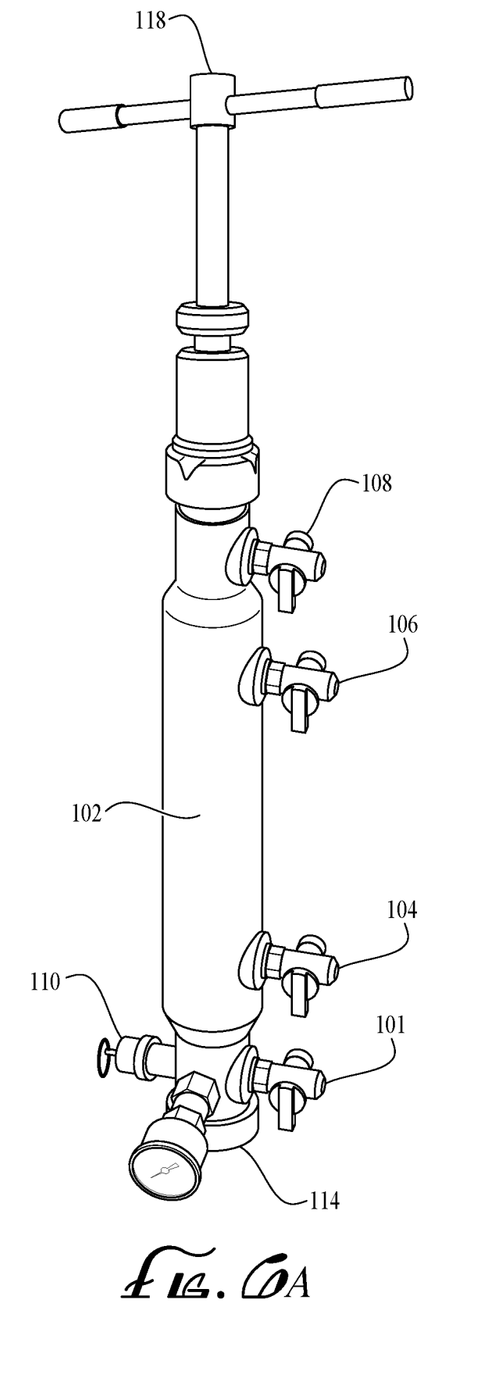
FIG. 6A shows the chamber of FIG. 1.
Figure 6B:
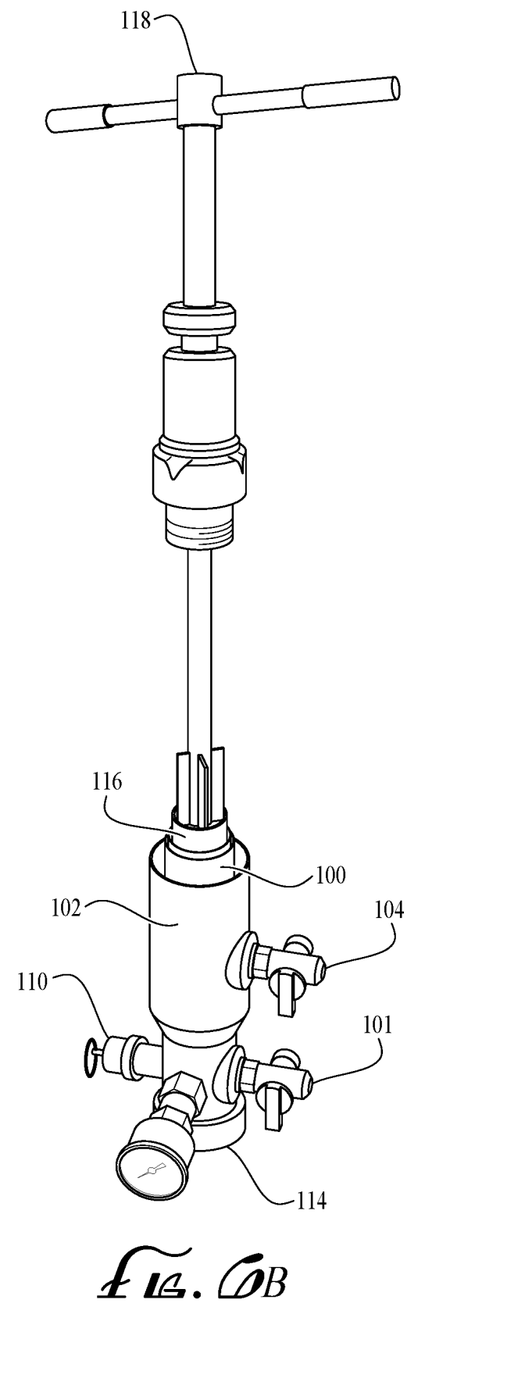
FIG. 6B shows the internal components of the chamber shown in FIG. 6A.

As shown in FIGS. 6A & 6B, the chamber 28 of FIG. 1 contains a chamber body 100 that is preferably of long and narrow dimensions. This configuration minimizes the distance between solids in the chamber 28 and coolant circulating through the jacket thereby facilitating cooling. In a preferred embodiment, the volume of the chamber 28 is 1.5 liters. Should the preferred embodiment be scaled up or down in size, the general ratio of the volume of the gas container 24 to the gas chamber 28 is preferably maintained at a 1:1.5 ratio.

This chamber body 100 is where the liquid gas meets solid materials and mixing occurs. The chamber body 100 has a chamber gas input valve 101. This valve serves two purposes. First, it is a site for vacuum attachment and vacuuming air from the chamber and for injecting the liquified natural gas into the chamber 28 from the gas storage container 24. The chamber cryogenic jacket 102 is mounted upon and surrounds the chamber 28. The chamber cryogenic jacket 102 has a chamber cryogenic jacket coolant intake valve 104 and a chamber jacket coolant output valve 106. The cryogenic coolant intake valve 104 is configured to be attached to the sixth hose 235, while the cryogenic coolant output valve 106 is configured to be attached to the seventh hose 237. The interior of the chamber body 100 may be lined with a polyethylene terephthalate layer 116 that acts as an anti-sparking layer. The polyethylene terephthalate layer 116 is fixed to the chamber by an adhesive and is configured to reduce friction generated by the rotation of the mixing handle 118. The chamber body 100 has a safety valve 110 which releases at 200 bar, which serves as a safety measure. If pressure from the system exceeds that limit the valve opens allowing gas to escape the chamber 28. The chamber body 100 should be able to withstand 1.5 times the safety valve capacity.

Figures 7A, 7B:
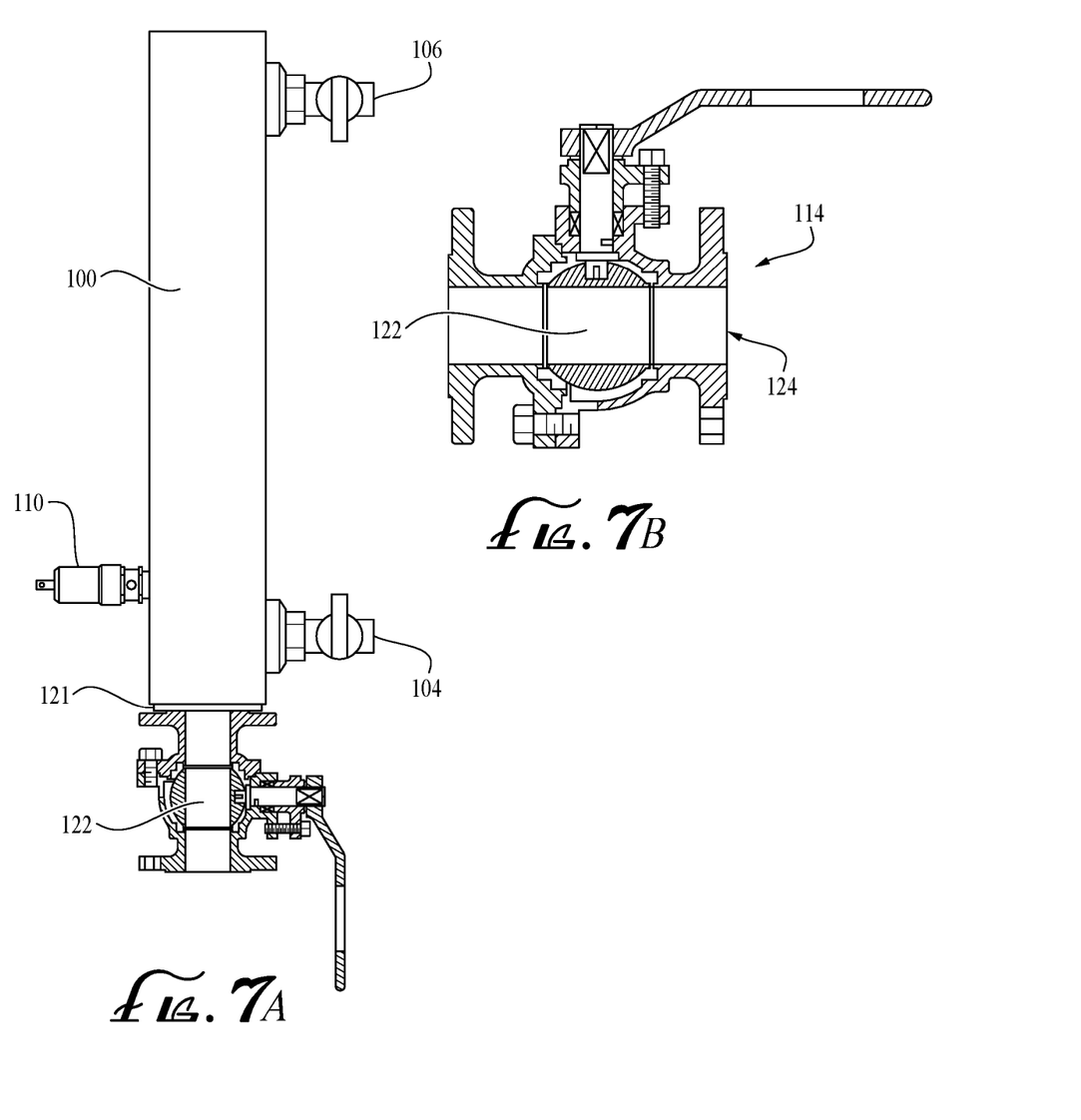
FIG. 7A shows the chamber and chamber base as shown in FIG. 1.
FIG. 7B shows the base of the chamber of FIG. 1.

As shown in FIGS. 7A and 7B, the chamber 28 contains a base 114 where solid material may enters and be removed from the chamber 28. The base 114 contains a ball valve 122. The base 114 contains a replaceable chamber door 124. The handle 118 contains a mechanical pressure seal 136. The chamber input valve 101 is lined with a vacuum filter 121. The vacuum filter 121 prevents the solid bed methane complex from exiting the chamber 28 during vacuum air removal. This base 114 is configured to accept a solid methane bed complex, further described below, for mixing with the liquified natural gas in the chamber 28.

Figure 8:
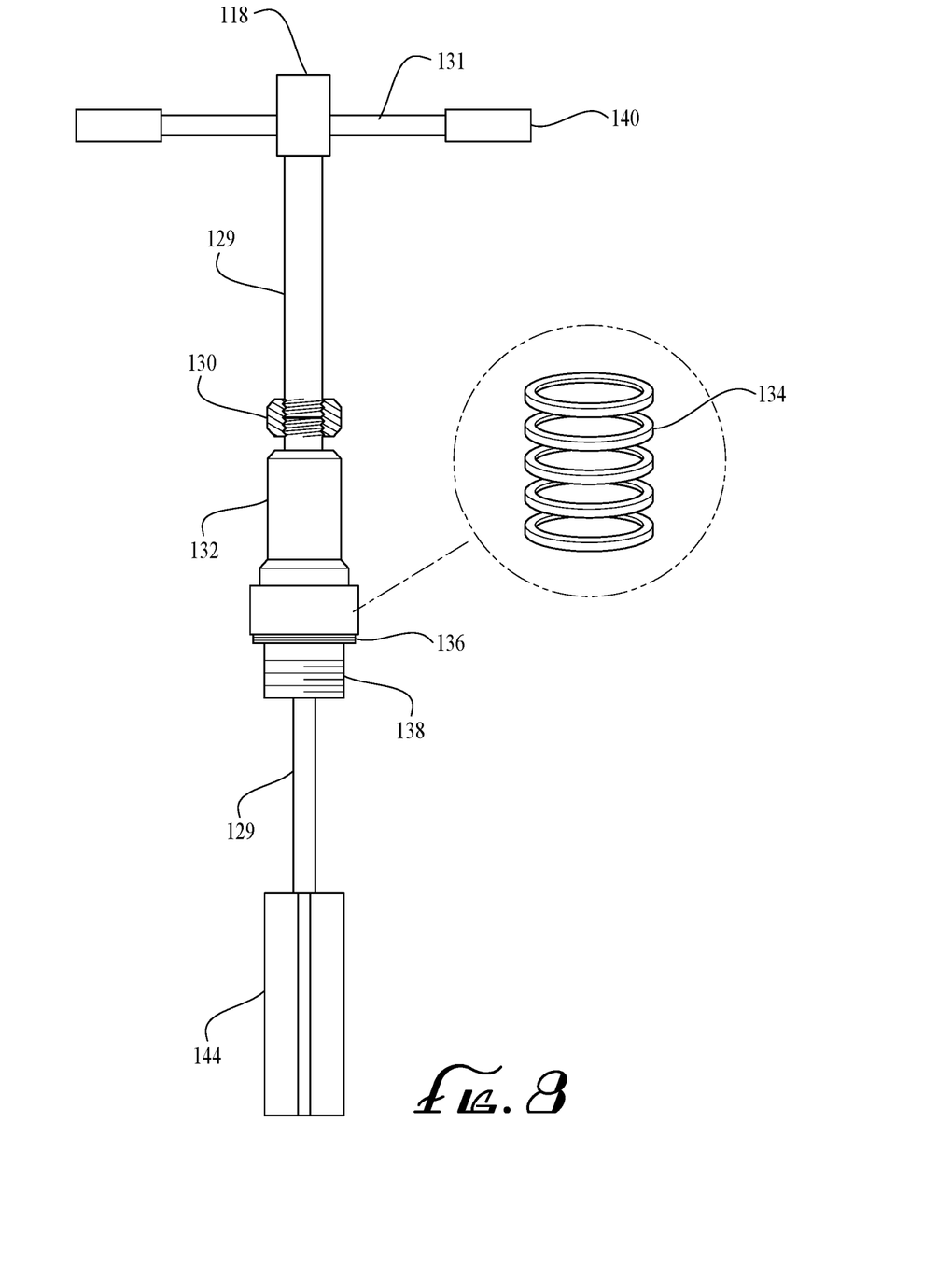
FIG. 8 shows an expanded view of the handle of the chamber of FIG. 1.

As shown in FIG. 8, the chamber 28 contains the mixer handle 118. The mixer handle 118 serves to mix and homogenize the content within the chamber 28, and runs along the interior of the chamber body 100. The mixer handle 118 comprises a hard shaft 129 with a rotating handle 131 on one end and a mixing impeller 144 on another end. A threaded coupling 130 on the shaft connects to a flange 132 which stabilizes the hard shaft 129. The flange 132 connects to the mechanical seal 136 that surrounds the hard shaft 129. The mechanical seal 136 may contain silicone washers 134. This combination of components serves to prevent gas escape at pressure. The hard shaft 129 contains a nut 138 that stabilizes the hard shaft 129. The nut 138 prevents the hard shaft 129 from deviating from position during mixing. A rotating grip 140 is mounted on the hard shaft 129 at the top of the hard shaft 129. An embodiment of the invention may have an internal mixer that is capable of being automatically rotated by the hard shaft 129, such that the mixing is performed automatically as opposed to manually.

A Method of Using an Apparatus for Making Solid Methane Gas

A general method of using the apparatus is also disclosed. The general method involves first placing natural gas within a drum 20. The next step involves opening a chamber door 124 located on the base 114 of the chamber 28 and placing within the chamber 28 the solid methane bed complex. Next, the chamber door 124 is closed and sealed. Then, air is removed from the chamber 28 by the vacuum 27 connected to the chamber gas input valve 101. At this step, the environment within the chamber body 100 includes the solid methane bed complex within a vacuum environment.

Once the solid methane bed complex is placed within the chamber 28, the cooling case 22 is filled with the coolant. The coolant may be made of ice and salt. In other embodiments the coolant may be made of refrigerant gases. In embodiments where refrigerant gases are used as the coolant, the coolant does not need to be cycled throughout the system and may be individually contained in each of the coolant cavity 38 of the cooling case 22, the gas storage container cryogenic jacket 40, and the chamber cryogenic jacket 102. As such, embodiment using refrigerant gases instead of ice and water do not need to be recirculated, and as such do not require coolant input and output valves on the cooling case 22, gas storage container cryogenic jacket 40, or chamber cryogenic jacket 102. While the aforementioned coolants are preferred, other coolants may be utilized without departing from the concepts disclosed herein.

The coolant output 35 is connected by the third hose 231 and fourth hose 233 to the gas storage container jacket coolant intake valve 46. The pump 26 lies at the end of the third hose 231. The gas storage jacket coolant output valve 48 is connected to the cooling case coolant intake 39 by the eighth hose 239. The coolant valves 46 and 48 are opened, and the pump 26 is engaged, thereby circulating coolant between the cooling case 22 and gas storage cryogenic jacket 40, as shown in FIG. 3. Cycling the coolant through this system keeps the coolant cold, keeping the natural gas in the gas storage container 24 liquid.

Next, the drum valve 21 is opened allowing gas to flow to the cooling case gas input 32. Gas then flows through the pipe 34 for indirect exposure to coolant in the coolant cavity 38. Piped gas exits the cooling case 22 at the cooling case gas output 36 then on to the manometer 112 housing a gas flow indicator 30. Gas then flows from the manometer 112 to the gas storage container 24.

The manometer 112 ensures primarily liquid, rather than gaseous, natural gas enters the gas storage container 24. The transparent chamber 112a on the manometer 112 permits an observer to detect the physical state of natural gas. In another embodiment, the manometer 112 can also automatically detect the physical state of natural gas. If gaseous natural gas is observed, the manometer gas release 112b is opened to release excess gaseous natural gas, then closed. In some embodiments, the excess gas that is released from the manometer gas release 112b may be recaptured and reinserted into the system, resulting in no waste. A large-scale embodiment of the apparatus may capture excess gaseous gas at the gas release 112b as well. Liquid natural gas flows until the gas flow indicator 30 indicates zero flow and a gas storage container temperature gauge 41 indicates freezing. Preferably, the temperature sought on the temperature gauge 41 is −20° C. In other embodiments, such as when a magnesium chloride salt is used as the base for the solid methane bed complex, the temperature sought may be between −10° C. and −20° C. These observations taken together indicate that liquified natural gas is inside the gas storage container 24.

The coolant circulating through the gas storage container 24 is then redirected to the chamber cryogenic jacket 102 surrounding the chamber 28 to keep the temperatures surrounding the chamber 28 at subzero Celsius conditions, preferably −20° C. The gas storage container cryogenic jacket intake valve 46 and gas storage container cryogenic jacket output 48 are closed. Then the fourth hose 233 connected at the gas storage jacket coolant intake valve 46 is replaced or shut off such that the coolant flows from the pump 26 through the sixth hose 235 to the chamber cryogenic jacket coolant intake valve 104. The seventh hose 237 connects the chamber cryogenic jacket coolant output valve 106 back to the coolant case 22 at coolant intake 37. The coolant valves are then reopened, and coolant circulates from the cooling case 22 through the chamber cryogenic jacket 102 and back in the same configuration as shown in FIG. 3, but with the chamber 28 used instead of the gas storage container 24. In some embodiments, the fluid pump 26 is configured to only be secured to either the gas storage cryogenic jacket 40 or the chamber cryogenic jacket 102, as described above. However, in other embodiments, such as the embodiment shown in FIG. 1A, the fluid pump 26 is configured to be secured to both the gas storage cryogenic jacket 40 and the chamber cryogenic jacket 102, such that the removal, replacement, or shutting down of the hoses is not necessary. In other embodiments, the shift of the coolant moving from the cooling case 22 to the gas storage cryogenic jacket 40 to the coolant flowing from the cooling case 22 to the chamber cryogenic jacket 102 may be facilitated by switching on and off valves located near the fluid pump 26.

The drum valve 21 is then closed. This stops any natural gas from flowing to the cooling case 22 and gas storage container 24 after filling the gas storage container 24 with liquid gas. The gas storage container gas output 53 of the gas storage container 24 and chamber gas input valve 101 are opened. When the chamber gas meter 112 reads zero flow the chamber 28 is full of liquified natural gas. All gas valves are closed, sealing the system.

The liquified natural gas in the chamber 28 is then mixed with the solid methane bed complex previously placed into the chamber 28 by rotating the mixer handle 118. Coolant circulates around the mixing chamber 28 for twenty-four hours maintaining subzero Celsius conditions in the chamber 28. In a preferred embodiment, the temperature will be maintained at −20° C. After twenty-four hours, the mixing is stopped, and a safety valve 110 is opened to release any excess gas. In another embodiment, the excess gas may be released from a gas release valve 108 on the chamber 28 and recaptured via a compressor, such that the excess gas can be recycled back into the system. Should any excess liquid natural gas be present, it may also be released by the gas release valve 108 and recaptured via the compressor. This configuration will result in no extra waste after the natural gas is solidified. The chamber door 124 is then opened to access the resulting solid doughy product. The remaining solid doughy product is removed, then drained and dried over speed dryer paper, preferably at subzero Celsius conditions. In the preferred embodiment, the solid doughy product is dried at a temperature of −4° C. and 0° C. In other embodiments, it is possible to dry the solid doughy product at room temperature. The resulting solid product is solidified methane gas that is now that is capable of storage and shipment without specialized equipment.

Method for Preparing Solid Methane Bed Complex

A method for preparing a solid methane bed complex (SMBC) is also disclosed. The solid methane bed complex is made by preparing a methane bed mix, which is selected from either a calcium sulfate mix formulation, calcium oxide mix formulation or magnesium chloride mix formulation. The methane bed mix is prepared by finely blending any one of a calcium sulfate formulation, calcium oxide formulation or magnesium chloride formulation for reversible production of solid gas.

The methane bed mix has any one of a calcium sulfate formulation, calcium oxide formulation or magnesium chloride formulation. The calcium sulfate bed mix formulation may include calcium sulfate, 2,3,4-trimethylpentane, silicon dioxide, magnesium chloride, Marble Dust, foamed concrete, nanomaterial, zinc oxide, calcium carbonate, zinc stearate, water, liquid natural gas, ethanol, red sulfur, colors, and empty gelatin capsules. The calcium oxide bed mix formulation may include calcium oxide, orpiment, silicon dioxide, magnesium chloride, foamed concrete, nanomaterial, zinc oxide, zinc stearate, water, liquid natural gas, calcium carbonate, ethanol, phosphate, red sulfur, colors, and empty gelatin capsules. The magnesium chloride formulation may include magnesium chloride, sodium chloride, zinc oxide, 2,3,4, trimethylpentane+paraffin, nanomaterial, zinc stearate, water, liquid natural gas, calcium carbonate, ethanol, red sulfur, phosphate, colors, and empty gelatin capsules.

Once one of the methane bed mixes is prepared, it will become the solid methane bed complex for placement into the chamber 28. The method of creating the solid methane bed complex is further discussed below.

Method for Making Solid Methane Bed Complex (SMBC)

A method for making solid methane bed complex involves preparing a methane bed mix by blending together reagents, except nanomaterials, adding required nanomaterials to said blend, and mixing until a consistent viscosity is reached. The methane bed mix may be selected from a calcium sulfate mix, a calcium oxide mix, or a magnesium chloride mix. Each of these mixes are described in detail below. Once the solid methane bed complex is prepared, the solid methane bed complex is placed into the chamber 28 for mixing with the liquified natural gas.

Methane Bed Calcium Sulfate Mix

A 1 kg methane bed calcium sulfate mix is made up of 500 grams calcium sulfate ($CaSO_4$); 12 grams of 2,3,4, trimethylpentane ($C_8H_{18}$); 18 grams of silicon dioxide ($SiO_2$); 24 grams of foamed concrete; 12 grams of magnesium chloride ($MgCl_2$); 6 grams of nanomaterials (4.5 g $KNO_3$+1.5 g NaCl); 10 grams of zinc oxide (ZnO); 50 grams of Marble Dust; 10 grams of zinc stearate ($Zn(C_{18}H_{35}O_2)_2$); 50 grams of water ($H_2O$); 300 grams of liquid natural gas ($CH_4$); 3 grams of calcium carbonate ($CaCO_3$); 2 milliliters of ethanol (EtOH); 2 grams of red sulfur; 1 gram of colors, and empty gelatin capsules. The reagents are combined by blending and may be added in any order so long as the base calcium sulfate is added to the blender first. These reagents are blended until the reagents are fully mixed, i.e., a consistent viscosity is reached.

Foamed concrete facilitates creation of interstitial cavities within the methane bed mix. Cavities create more surface area to promote gas retention. 2,3,4, trimethylpentane is used for its anti-knocking materials to prevent from going out. Nanomaterials (potassium nitrate+sodium chloride) stabilize the methane bed mix, increasing durability of the solid methane bed complex. The nanomaterials are packed into empty gelatin capsules. The capsules serve to delay nanomaterial interaction with water. As the mix is stirred the nanomaterials are released. This promotes uniform distribution throughout the mix. Zinc oxide serves to whiten the product. Calcium carbonate has adhesive properties and serves as a bonding agent within the mix. Zinc stearate serves as a lubricant facilitating mix movement during stirring. It also makes the product more pleasant to touch. Liquid natural gas is the methane source. Silicon dioxide is used for anti-clumping properties which facilitate mixing.

Once all of the reagents are fully mixed, the methane bed mix having the calcium sulfate base will be one form of the solid methane bed complex. This complex is configured to then be placed into the chamber 28 for mixing with the liquified natural gas to form solid natural gas.

Methane Bed Calcium Oxide Mix

A 1 kg methane bed calcium oxide mix is made up of 500 grams calcium oxide (CaO); 60 grams orpiment ($As_2S_3$); 18 grams silicon dioxide ($SiO_2$); 12 grams of magnesium chloride ($MgCl_2$); 24 grams foamed concrete; 6 grams nanomaterials (4.5 g $KNO_3$+1.5 g NaCl); 10 grams zinc oxide (ZnO); 10 grams zinc stearate ($Zn(C_{18}H_{35}O_2)_2$); 50 grams water ($H_2O$); 300 grams liquid natural gas ($CH_4$); 3 grams of calcium carbonate ($CaCo_3$); 2 milliliters of ethanol (EtOH); 2 grams of phosphate ($PO_4^{3-}$); 2 grams of red sulfur; 1 gram of colors, and empty gelatin capsules. The reagents are combined by this blending, and may be added in any order so long as the base calcium oxide is added first. These reagents are blended until the reagents are fully mixed, i.e., a consistent viscosity is reached.

Reagents in the methane bed calcium oxide mix identical reagents in mixes above serve the same purpose. Orpiment reduces the ignition temperature. Once all of the reagents are fully mixed, the methane bed mix having the calcium oxide base will be another form of the solid methane bed complex.

This complex is configured to then be placed into the chamber 28 for mixing with the liquified natural gas to form solid natural gas.

Methane Bed Magnesium Chloride Mix 1 kg methane bed magnesium chloride mix is made up of 200 grams magnesium chloride ($MgCl_2$); 100 grams Sodium Chloride (NaCl); 10 grams zinc oxide (ZnO); 5 grams 2,3,4, trimethylpentane ($C_8H_{18}$); 5 grams of paraffin ($C_nH_{2n+2}$); 6 grams nanomaterials (4.5 g $KNO_3$+1.5 g NaCl); 10 grams zinc stearate ($Zn(C_{18}H_{35}O_2)_2$); 40 grams water ($H_2O$); 600 grams liquid natural gas ($CH_4$); 12 grams of calcium carbonate ($CaCo_3$); 2 milliliters of ethanol (EtOH); 5 grams of red sulfur; 4 grams of phosphate ($PO_4^{3-}$); 1 gram of colors, and empty gelatin capsules. The reagents are combined by blending and may be added in any order so long as the base magnesium chloride is added first, and the 10 grams of 2,3,4 trimethylpentane and 5 grams of parrafin are premixed prior to addition to the blender. These reagents are blended until the reagents are fully mixed, i.e., a consistent viscosity is reached.

Reagents in the methane bed magnesium chloride mix identical to reagents in mixes above serve the same purpose. Once all of the reagents are fully mixed, the methane bed mix having the magnesium chloride base will be another form of the solid methane bed complex. This complex is configured to then be placed into the chamber 28 for mixing with the liquified natural gas to form solid natural gas.

For each of the aforementioned mixes (i.e., the calcium sulfate mix, the calcium oxide mix, and the magnesium chloride mix), the disclosed quantities of reagents must be used to produce 1 kg of the sought mix. Should higher or lower quantities of the resulting mixtures be sought, the quantities of the reagents should be increased or decreased at the same ratios noted above. For example, if 2 kg of calcium sulfate mix is sought, each reagent quantity listed above should be doubled. However, if 0.5 kg of the calcium sulfate mix is sought, each reagent quantity should be halved. As such, any quantity of reagents may be used so long as they match the ultimate ratios of reagents to final product disclosed above. This additionally holds true for the scale of the apparatus itself. Each of the disclosed dimensions and quantities above will ultimately result in 1 kg of solid methane gas being removed from the chamber 28 that is stable at room temperature, and thus can be stored and transported without specialized equipment.

What is claimed is:

1. A composition of solid methane comprising:
   a quantity of liquefied methane;
   a methane bed complex having a calcium sulfate bed complex formulation comprising calcium sulfate ($CaSo_4$), 2,3,4-trimethylpentane ($C_8H_{18}$), silicon dioxide ($SiO_2$), foamed concrete, magnesium chloride ($MgCl_2$), nanomaterials comprising potassium nitrate ($KNO_3$) and sodium chloride (NaCl), zinc oxide (ZnO), marble dust, zinc stearate ($Zn(C_{18}H_{35}O_2)_2$), water ($H_2O$), calcium carbonate ($CaCO_3$), ethanol (EtOH), and red sulfur ($S_{16}^{2+}$); and
   wherein the quantity of liquified methane and the methane bed complex have been mixed at sub-zero degrees Celsius.

2. The composition of claim 1 wherein relative quantities of the liquified methane and the calcium sulfate bed complex formulation, per 1 kg, comprises substantially 500 grams of the calcium sulfate, 12 grams of the 2,3,4-trimethylpentane, 18 grams of the silicon dioxide, 24 grams of the foamed concrete, 12 grams of the magnesium chloride, 6 grams of the nanomaterials, 10 grams of the zinc oxide, 50 grams of the marble dust; 10 grams of the zinc stearate, 50 grams of the water, 300 grams of the liquid methane, 3 grams of the calcium carbonate, 2 milliliters of the ethanol, and 2 grams of the red sulfur.

3. The compound of claim 2 further comprising 1 gram of a colorant.

4. The compound of claim 1 wherein the nanomaterials are packed into gelatin capsules to delay interactions between the nanomaterials and the water.

5. The compound of claim 1 wherein the calcium sulfate bed complex formulation further comprises a colorant.

6. A composition of solid methane comprising:
   a quantity of liquified methane;
   a methane bed complex having a calcium oxide bed complex formulation comprising calcium oxide (CaO), orpiment ($As_2S_3$), silicon dioxide ($SiO_2$), magnesium chloride ($MgCL_2$), foamed concrete, nanomaterials comprising potassium nitrate ($KNO_3$) and sodium chloride (NaCl), zinc oxide (ZnO), zinc stearate ($Zn(C_{18}H_{35}O_2)_2$), water ($H_2O$), calcium carbonate ($CaCO_3$), ethanol (EtOH), phosphate ($PO_4^{3-}$), and red sulfur ($S_{16}^{2+}$); and
   wherein the quantity of liquified methane and the methane bed complex have been mixed at sub-zero degrees Celsius.

7. The composition of claim 6 wherein relative quantities of the liquified methane and the calcium oxide bed complex formulation, per 1 kg, comprises substantially 500 grams of the calcium oxide, 60 grams of the orpiment, 18 grams of the silicon dioxide, 12 grams of the magnesium chloride, 24 grams of the foamed concrete, 6 grams of the nanomaterials, 10 grams of the zinc oxide, 10 grams of the zinc stearate, 50 grans of the water, 300 grams of the liquid methane, 3 grams of the calcium carbonate, 2 milliliters of the ethanol, 2 grams of the phosphate, and 2 grams of the red sulfur.

8. The compound of claim 7 further comprising 1 gram of a colorant.

9. The compound of claim 6 wherein the nanomaterials are packed into gelatin capsules to delay interactions between the nanomaterials and the water.

10. The compound of claim 6 wherein the calcium oxide bed complex formulation further comprises a colorant.

11. A composition of solid methane comprising:
    a quantity of liquified methane;
    a methane bed complex having a magnesium chloride bed complex formulation comprising magnesium chloride ($MgCl_2$), sodium chloride (NaCl), zinc oxide (ZnO), 2,3,4-trimethylpentane ($C_8H_{18}$), paraffin ($C_nH_{2n+2}$), nanomaterials comprising potassium nitrate ($KNO_3$) and sodium chloride (NaCl), zinc stearate ($Zn(C_{18}H_{35}O_2)_2$), water ($H_2O$), calcium carbonate ($CaCo_3$), ethanol (EtOH), red sulfur ($S_{16}^{2+}$), and phosphate ($PO_4^{3-}$); and
    wherein the quantity of liquified methane and the methane bed complex have been mixed at sub-zero degrees Celsius.

12. The composition of claim 11 wherein relative quantities of the liquified methane and the magnesium chloride bed complex formulation, per 1 kg, comprises substantially 200 grams of the magnesium chloride, 100 grams of the sodium chloride, 10 grams of the zinc oxide, 5 grams of the 2,3,4-trimethylpentane, 5 grams of the paraffin, 6 grams of the nanomaterials, 10 grams of the zinc stearate, 40 grams of the water, 600 grams of the liquid methane, 12 grams of the calcium carbonate, 2 milliliters of the ethanol, 5 grams of the red sulfur, and 4 grams of the phosphate.

13. The compound of claim 12 further comprising 1 gram of a colorant.

14. The compound of claim 11 wherein the nanomaterials are packed into gelatin capsules to delay interactions between the nanomaterials and the water.

15. The compound of claim 11 wherein the magnesium chloride bed complex formulation further comprises a colorant.

\* \* \* \* \*